United States Patent [19]

Rizkalla

[11] Patent Number: 4,540,811

[45] Date of Patent: Sep. 10, 1985

[54] PREPARATION OF CARBOXYLIC ACID ESTERS

[75] Inventor: Nabil Rizkalla, River Vale, N.J.

[73] Assignee: The Halcon SD Group, Inc., New York, N.Y.

[21] Appl. No.: 431,531

[22] Filed: Sep. 30, 1982

[51] Int. Cl.$^3$ .................................... C07C 67/38
[52] U.S. Cl. .................... 560/233; 260/410.5; 260/410.9 N; 260/410.9 R; 560/8; 560/100; 560/103; 560/104; 560/106; 560/107; 560/113; 560/114; 560/130; 560/138; 560/139; 560/206
[58] Field of Search ............... 560/233, 100, 101, 105, 560/114, 206, 8, 103, 104, 106, 107, 113, 130, 138, 139; 260/410.9 R, 410.5, 410.9 N

[56] References Cited

U.S. PATENT DOCUMENTS

| | | | |
|---|---|---|---|
| 2,868,813 | 1/1959 | Heisler | 560/233 |
| 3,755,421 | 8/1973 | Fenton et al. | 560/233 |
| 4,238,357 | 12/1980 | Pesa et al. | 560/233 |
| 4,354,036 | 10/1982 | Rizkalla | 560/101 |

FOREIGN PATENT DOCUMENTS 2329577  1/1975  Fed. Rep. of Germany ...... 560/233

Primary Examiner—Natalie Trousof
Assistant Examiner—Patricia M. Scott
Attorney, Agent, or Firm—William C. Long; Riggs T. Stewart; Harold N. Wells

[57] ABSTRACT

A carboxylic acid esters, such as methyl propionate, is prepared by carbonylation of an olefin, such as ethylene, in the presence of an alcohol by the use of a molybdenum-nickel-alkali metal, a tungsten-nickel-alkali metal or a chromium nickel-alkali metal co-catalyst and in the presence of a halide.

4 Claims, No Drawings

PREPARATION OF CARBOXYLIC ACID ESTERS

This invention relates to the preparation of carboxylic acid esters, more particularly mono-carboxylic acid esters, and especially lower alkanoic acid esters, such as propionic acid esters, by the carbonylation of olefins in the presence of an alcohol.

Carboxylic acid esters have been known as industrial chemicals for many years and large amounts are used in the manufacture of various products. Producing carboxylic acid esters by the action of carbon monoxide upon olefins (carbonylation) has been described in various patents by processes involving several types of catalysts. For example, Slaugh U.S. Pat. No. 3,168,553 shows the reaction of carbon monoxide with an olefinic hydrocarbon in the presence of alcohols by using a Group VIIIb transition metal carbonyl catalyst which contains cobalt, ruthenium, rhodium or iridium in complex combination with carbon monoxide and a trialkyl phosphorus. Anderson et al. U.S. Pat. No. 3,040,090 reacts carbon monoxide, an ethylenically-unreacted compound and an alcohol in the presence of a Group VIII noble metal chelate. Morris et al. U.S. Pat. No. 3,917,677 also shows a process involving a reaction among carbon monoxide, ethylenically-unsaturated compounds and alcohols which is characterized by using a catalyst containing a rhodium compound and a tertiary organo-phosphorus component. This patent contains a discussion of the prior art and the limitations of the prior art procedures, particularly, the poor yields obtainable with them. Furthermore, the prior art process, in general, require relatively high pressures. Even though improved yields are apparently obtained by the process of U.S. Pat. No. 3,917,677, that process requires the use of a very expensive Group VIII noble metal catalyst, i.e., a rhodium catalyst.

In my co-pending application Ser. No. 267,974, filed May 28, 1981 and entitled "Preparation of Carboxylic Acid Esters", U.S. Pat. No. 4,354,036, there is disclosed a related process for the carbonylation of olefins to produce carboxylic acid esters which uses a molybdenumnickel or tungsten-nickel co-catalyst in the presence of a promoter comprising an organo-phosphorus or an organonitrogen compound, such as a phosphine or a tertiary amine. While this process involves nickel catalysts which make possible carbonylation of olefins at modest pressures without requiring the use of a noble metal catalyst, and while this process is highly effective for its intended purpose, there is room for improvement in terms of reaction rate and productivity without needing to use organic promoters.

It is accordingly an object of the present invention to provide an improved process for the manufacture of carboxylic acid esters, especially lower alkanoic acid esters, such as propionic acid esters, e.g., methyl propionate, which requires neither high pressures nor Group VIII noble metals and makes possible the production of carboxylic acid esters in high yields in short reaction times without needing to use organic promoters.

In accordance with the invention, carbonylation of an olefin is carried out by using a molybdenum-nickel-alkali metal, a tungsten-nickel-alkali metal or a chromium-nickel-alkali metal co-catalyst in the presence of a halide, preferably an iodide, a bromide, and/or a chloride, especially an iodide, and in the presence of an alcohol. The surprising discovery has been made that this co-catalyst system, in an environment of the character indicated, makes possible the carbonylation of olefins not only at relatively low pressures but with rapid, high yield production of carboxylic acid esters.

The outstanding effectiveness of the catalyst system of the process of this invention is particularly surprising in view of the experimental data reported in European published application No. 0 035 458 which shows the carbonylation of methanol to produce acetic acid and in which experiments using nickel in combination with molybdenum or tungsten or chromium showed absolutely no reaction even after two hours. It has also been observed that when nickel-based catalysts are ordinarily used in carbonylation reactions, there is a tendency for the nickel components to be volatilized and to appear in the vapors from the reaction. It has been surprisingly found that, with the catalyst system of this invention, the volatility of the nickel is strongly suppressed and a highly-stable catalyst combination results, especially in the case of the molybdenum-containing co-catalyst, which is the preferred co-catalyst.

Thus, in accordance with the invention, carbon monoxide is reacted with an olefin such as a lower alkene in the presence of an alcohol, e.g., methanol, to produce a carboxylic acid ester, such as a lower alkanoic acid ester, e.g., methyl propionate, the carbonylation taking place in the presence of a halide, e.g., a hydrocarbyl halide, especially a lower alkyl halide, such as ethyl iodide, and in the presence of the co-catalyst and promoter combination which has been identified above. Propionic acid esters, for example, can be effectively prepared in a representative case by subjecting ethylene to carbonylation in the presence of alcohols.

In like manner, esters of other carboxylic acids can be produced by carbonylating the corresponding alkene in the presence of an alcohol.

The reactant olefin may be any ethylenically unsaturated hydrocarbon having from 2 to about 25 carbon atoms, preferably from 2 to about 15 carbon atoms. The ethylenically unsaturated compound has the following general structure:

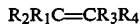

wherein $R_1$, $R_2$, $R_3$ and $R_4$ are hydrogen or the same or different alkyl, cycloalkyl, aryl, alkaryl, aralkyl or wherein one of said $R_1$ and $R_2$ and one of said $R_3$ and $R_4$ together form a single alkylene group having from 2 to about 8 carbon atoms. $R_1$, $R_2$, $R_3$ and $R_4$ can be branched and can be substituted with substituents which are inert in the reactions of the invention.

Examples of useful ethylenically unsaturated hydrocarbons are ethylene, propylene, butene-1, butene-2, 2-methylbutene-1, cyclobutene, hexene-1, hexene-2, cyclohexene, 3-ethylhexene-1, isobutylene, octene-1,2-methylhexene-1, ethylcyclohexene, decene-1, cycloheptene, cyclooctene, cyclononene, 3,3-dimethylnonene-1, dodecene-1, undecene-3, 6-propyldecene-1, tetradecene-2, 3-amyldecene-1, etc., hexadecene-1, 4-ethyltridecene-1, octadecene-1, 5,5-dipropyldodecene-1, vinylcyclohexane, allylcyclohexane, styrene, p-methylstyrene, alpha-methylstyrene, p-vinylcumene, beta-vinylnaphthalene, 1,1-diphenylethylene, allylbenzene, 6-phenylhexene-1, 1,3-diphenylbutene-1, 3-benzylheptene-1, divinylbenzene; 1-allyl-3-vinylbenzene, etc. Of the olefins referred to above, the alpha hydrocarbon olefins and olefins having 2 to about 10 carbon atoms are preferred, e.g., ethylene, propylene, butene-1, hexene-1, heptene-1, octene-1, and the like, i.e., wherein $R_1$, $R_2$, $R_3$ and $R_4$ are hydrogen or alkyl groups totalling 1-8 carbon atoms, preferably the lower alkenes, i.e., alkenes of 2 to 6 carbon atoms, especially ethylene.

The reactant alcohol may be in general any alcohol having the formula ROH, wherein R is alkyl, cycloalkyl, aryl, alkaryl or aralkyl or mixtures thereof; preferably R has 1 to about 18 carbons and most preferably R is alkyl having 1 to about 12 carbons, e.g., methyl, ethyl, propyl, butyl, isobutyl, pentyl, hexyl, nonyl, and the like, or is aralkyl with 7 to about 14 carbons, e.g., benzyl, phenethyl, and the like.

Examples of suitable alcohols include methanol, ethanol, propanol, isopropanol, butanol, tertiary butanol, pentanol, hexanol, 2-ethylhexanol, octanol, decanol, 6-pentadecanol, cyclopentanol, methylcyclopentanol, cyclohexanol, benzyl alcohol, alpha alpha-dimethyl benzyl alcohol, alpha-ethylphenethyl alcohol, naphthyl carbinol, xylyl carbinol, tolyl carbinol, and the like.

In the most preferred embodiment of the invention, carbon monoxide is reacted with ethylene and methanol in the presence of the co-catalyst-halide system of the character described above to produce methyl propionate in a reaction which may be expressed as follows:

$$C_2H_4 + CO + CH_3OH \rightarrow C_2H_5COOCH_3$$

The reaction is preferably carried out in the liquid phase. Carbon monoxide is removed in the vapor phase along with unreacted olefin when the olefin is normally gaseous, e.g., ethylene, and, if desired, recycled. Normally liquid and relatively volatile components such as alkyl halide, normally-liquid unreacted olefin and the alcohol, and any by-products, present in the final product mixture can be readily removed and separated from each other and from the catalyst components as by distillation, for recycling. The net yield of product is substantially exclusively the desired carboxylic acid ester. Most preferably the liquid phase reaction is carried out under boiling conditions and all volatile components are removed in the vapor phase, leaving the catalyst in the reactor. The reaction is suitably carried out in a reaction zone to which the carbon monoxide, the olefin, the alcohol, the halide, and the co-catalyst are fed.

As will be apparent from the foregoing equation, a carbonylation reaction of the character described selective to a carboxylic acid ester requires at least one mol of carbon monoxide and one mol of alcohol per mol (equivalent) of ethylenically-unsaturated linkage reacted.

In carrying out the process of the invention, a wide range of temperatures, e.g., 25° to 350° C. are suitable but temperatures of 100° to 250° C. are preferably employed and the more preferred temperatures generally lie in the range of 125° to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typically residence times, by way of example, will generally fall in the range of 0.1 to 20 hours. The reaction is carried out under superatmospheric pressure but, as previously mentioned, it is a feature of the invention that excessively high pressures, which require special high-pressure equipment, are not necessary. In general, the reaction is effectively carried out by employing a carbon monoxide partial pressure which is preferably at least 15 but less than 2,000 psi, most preferably 15 to 1,000 psi and particularly 30 to 200 psi, although CO partial pressures of 1 to 5,000 or even up to 10,000 psi can also be employed. By establishing the partial pressure of carbon monoxide at the values specified, adequate amounts of this reactant are always present. The total pressure is, of course, that which will provide the desired carbon monoxide partial pressure and preferably it is that required to maintain the liquid phase and, in this case, the reaction can be advantageously carried out in an autoclave or similar apparatus. At the end of the desired residence time the reaction mixture is separated into its several constituents, as by distillation. Preferably, the reaction product is introduced into a distillation zone which may be a fractional distillation column, or a series of columns, effective to separate the volatile components from the product ester and to separate the product ester from the less volatile catalyst components of the reaction mixture. The boiling points of the volatile components are sufficiently far apart that their separation by conventional distillation presents no particular problem. Likewise, the higher-boiling organic components can be readily distilled away from the metal catalyst components. The thus recovered cocatalyst, including the halide component, and unreacted alcohol, can then be combined with fresh amounts of olefin, carbon monoxide and alcohol and reacted to produce additional quantities of carboxylic acid ester. When the reaction is run under boiling conditions, the effluent is entirely in the vapor phase and, after condensation, the components can be separated from each other as described above.

Although not necessary, the process can be carried out in the presence of a solvent or diluent. The presence of a solvent or diluent, preferably the product ester or its acid, e.g., methyl propionate or propionic acid in the case of ethylene carbonylation, will make it possible to employ more moderate total pressures. Alternatively, the solvent or diluent may be any organic solvent which is inert in the environment of the process such as hydrocarbons, e.g., octane, benzene, toluene, xylene and tetralin, or carboxylic acids. A carboxylic acid, if used, should preferably correspond to the ester being produced since, it is preferred that the solvent be one that is indigenous to the system, e.g., propionic acid in the case of ethylene carbonylation, although other carboxylic acids such as acetic acid can also be used. A solvent or diluent, when not the product itself, is suitably selected which has a boiling point sufficiently different from the desired product in the reaction mixture so that it can be readily separated. It is preferred to add the alcohol gradually to the reaction zone to minimize by-product formation. In this case, a solvent is desired and preferably it is one that is indigenous to the system, such as propionic acid or methyl propionate in the case of ethylene carbonylation. Mixtures can be used.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. Hydrogen which may be present as an impurity is not objectionable and even may tend to stabilize the catalyst. Indeed, in order to obtain low CO partial pressures, the CO fed may be diluted with hydrogen or any inert gas such as those mentioned above.

The diluent gas, e.g., hydrogen, may generally be used in an amount up to about 95%, if desired.

The co-catalyst components can be employed in any convenient form, viz., in the zero valent state or in any higher valent form. For example, the nickel and the molybdenum, tungsten or chromium can be the metals themselves in finely divided form, or a compound, both organic or inorganic, which is effective to introduce the co-catalyst components into the reaction system. Thus, typical compounds include the carbonate, oxide, hydroxide, iodide, chloride, oxyhalide, hydride, lower alkoxide(methoxide), phenoxide, or Mo, W, Cr or Ni carboxylates wherein the carboxylate ion is derived from an alkanoic acid of 1 to 20 carbon atoms, such as acetates, butyrates, decanoates, laurates, benzoates, and the like. Similarly, complexes of any of the co-catalyst components can be employed, e.g., carbonyls and metal alkyls as well as chelates, association compounds and enol salts. Examples of other complexes include bis-(triphenylphosphine)nickel dicarbonyl, tricyclopentadienyl trinickel dicarbonyl, tetrakis(triphenylphosphite)-nickel, and corresponding complexes of the other components, such as molybdenum hexacarbonyl and tungsten hexacarbonyl.

Particularly preferred are the elemental forms, compounds which are halides, especially iodides, and organic salts, e.g., salts of the monocarboxylic acid corresponding to the acid being produced.

The alkali metal components, e.g., a metal of Group IA of the Periodic Table such as lithium, potassium, sodium, and cesium, is suitably employed as a compound, especially a salt, and most preferably a halide, i.e., an iodide. The preferred alkali metal is lithium. The alkali metal component can, however, also be employed as the hydroxide, carboxylate, alkoxide or in the form of other convenient compounds such as are referred to above in connection with the other co-catalyst components, and typical alkali metal components are illustrated by sodium iodide, potassium iodide, cesium iodide, lithium iodide, lithium bromide, lithium chloride, lithium acetate, and lithium hydroxide.

It will be understood that the above-mentioned compounds and complexes are merely illustrative of suitable forms of the several co-catalyst components and are not intended to be limiting.

The specified co-catalyst components employed may contain impurities normally associated with the commercially available metal or metal compounds and need not be purified further.

The amount of each co-catalyst component employed is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each catalyst component is employed in the amount of 1 millimol to 1 mol per liter of reaction mixture, preferably 15 millimoles to 500 millimoles per liter and most preferably 15 millimoles to 150 millimoles per liter.

The ratio of nickel to the molybdenum, tungsten, or chromium co-catalyst component can vary. Typically, it is one mol of the nickel component per 0.01 to 100 mols of the second co-catalyst component, i.e., the molybdenum, tungsten, or chromium component, preferably the nickel component is used in the amount of 1 mol per 0.1 to 20 mols, most preferably 1 mol per 1 to 10 mols of the second co-catalyst component. Similarly, the ratio of nickel to the alkali metal component can vary, e.g. one mol of nickel per 1 to 1000 mols of alkali metal component, preferably 10 to 100 and most preferably 20 to 50.

The amount of halide component may also vary widely but, in general, it should be present in an amount of at least 0.1 mol (expressed as elemental halogen) per mol of nickel. Typically, there are used 1 to 100 mols of the halide per mol of nickel, preferably 2 to 50 mols per mol. Ordinarily, more than 200 mols of halide per mol of nickel are not used. It will be understood, however, that the halide component does not have to be added to the system as a hydrocarbyl halide but may be supplied as another organic halide or as the hydrohalide or other inorganic halide, e.g., a salt, such as the alkali metal or other metal salt, or even as elemental halogen, e.g., iodine or bromine.

As previously mentioned, the catalyst system of this invention comprises a halide, especially an iodide, component and a molybdenum-nickel-alkali metal, tungsten-nickel-alkali metal, or chromium-nickel-alkali metal co-catalyst component. The catalyst system of this invention permits the production of carboxylic acid esters in high yields in short reaction times without the use of Group VIII noble metals, and the presence of the alkali metal component together with the molybdenum, tungsten or chromium component makes possible good results with relatively small amounts of co-catalyst components and reduced quantities of nickel in comparison with prior art processes involving a nickel-containing catalyst.

A particular embodiment of the catalyst comprising the molybdenum-nickel-alkali metal, tungsten-nickel-alkali metal, or chromium-nickel-alkali metal co-catalyst component and the halide component can be represented by the following formula: X:T:Z:Q, wherein X is molybdenum, tungsten or chromium, T is nickel, X and T being in zero valent form or in the form of a halide, an oxide, a carboxylate of 1 to 20 carbon atoms, a carbonyl or an hydride; Z is a halide source which is hydrogen halide, halogen, an alkyl halide wherein the alkyl group contains 1 to 20 carbon atoms or an alkali metal halide, and Q is the alkali metal component. The preferred alkali metal is lithium as previously indicated, and is in the form of an iodide, a bromide, a chloride or a carboxylate as defined for X and T, the molar ratio of X to T being 0.1–10:1, the molar ratio of X+T to Q being 0.1–10:1, and the molar ratio of Z to X+T being 0.01–0.1:1.

It will be apparent that the above-described reaction lends itself readily to continuous operation in which the reactants and catalysts are continuously supplied to the appropriate reaction zone and the reaction mixture continuously distilled to separate the volatile organic constituents and to provide a net product consisting essentially of carboxylic acid with the other organic components being recycled and, in a liquid-phase reaction a residual catalyst containing fraction also being recycled.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported, i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst component. Concentrations upon the carrier may vary widely, e.g., 0.01 weight percent to 10 weight percent, or higher. Typical operating conditions for vapor-phase operation are a temperature of 100° to 350° C., preferably 150° to 275° C. and most preferably 175° to 255° C., a pressure of 1 to 5,000 p.s.i.a., preferably 59 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$ (STP). In the case of a supported catalyst, the iodide component is included with the reactants and not on the support.

The following examples will serve to provide a fuller understanding of the invention, but it is to be understood that they are given for illustrative purposes only, and are not to be construed as limitative of the invention. In the examples, all parts are by weight, unless otherwise indicated.

EXAMPLE 1

In this example, a magnetically-stirred Hastelloy Parr bomb with a glass liner was employed as the reaction vessel. The bomb was charged with tetrahydrofuran (57 parts), ethyl iodide (12 parts), nickel iodide (0.68 parts), molybdenum hexacarbonyl (1.4 parts), lithium iodide (13.6 parts) and methanol (16 parts), was swept out with argon and pressured to 400 p.s.i.g. with carbon monoxide. The vessel was heated to 180° C. with stirring and then the vessel was charged with ethylene to bring the pressure up to 800 p.s.i.g. The pressure was maintained at 800 p.s.i.g. by recharging carbon monoxide and ethylene in equal amounts when needed and the temperature was maintained at 180° C. After ½ hour reaction, G.C. analysis of the reaction effluent showed that methyl propionate had been produced at the rate of 1.75 mols per liter per hour.

EXAMPLE 2

Example 1 was repeated except that the molybdenum hexacarbonyl was replaced by an equal amount of tungsten hexacarbonyl. It was found that methyl propionate had been formed at the rate of 0.55 mol per liter per hour.

EXAMPLE 3

Example 1 was repeated but the molybdenum hexacarbonyl was replaced by an equal quantity of chromium hexacarbonyl. Analysis showed that methyl propionate had been formed at the rate of 0.52 mole per liter per hour.

COMPARATIVE EXAMPLE

Example 1 was again repeated but the molybdenum hexarcarbonyl was omitted from the charge. Analysis showed that no methyl propionate had been formed.

What is claimed is:

1. A process for the preparation of a carboxylic acid ester by carbonylation which comprises reacting under superatmospheric pressure an olefin in the absence of oxygen with carbon monoxide in the presence of an alcohol, in the presence of a non-Group VIII-noble-metal-containing catalyst consisting essentially of a molybdenum-nickel-alkali metal, a tungsten-nickel-alkali metal or a chromium-nickel alkali metal co-catalyst component, and being free from organic promoters, and in the presence of a halide.

2. A process as defined in claim 1, wherein the co-catalyst component consists essentially of molybdenum-nickel-alkali metal.

3. A process as defined in claim 1 wherein the alkali metal is lithium.

4. A process as defined in claim 3, wherein the cocatalyst consists essentially of molybdenum-nickel-alkali metal.

* * * * *